United States Patent [19]

Debono et al.

[11] Patent Number: 5,534,420
[45] Date of Patent: Jul. 9, 1996

[54] BIOTRANSFORMATION OF GLYCOPEPTIDE ANTIBIOTICS

[75] Inventors: Manuel Debono, Indianapolis; Robert M. Logan, Greenwood; Gary G. Marconi, Indianapolis; R. Michael Molloy, Danville; Milton J. Zmijewski, Jr., Carmel, all of Ind.

[73] Assignee: Eli Lilly and Company, Indianapolis, Ind.

[21] Appl. No.: 444,119

[22] Filed: May 18, 1995

Related U.S. Application Data

[62] Division of Ser. No. 117,376, Sep. 3, 1993, abandoned, which is a continuation of Ser. No. 627,628, Dec. 13, 1990, abandoned, which is a continuation of Ser. No. 225,690, Jul. 28, 1988, abandoned.

[51] Int. Cl.$^6$ .............................. C12N 1/20; C12P 21/00
[52] U.S. Cl. .................... 435/71.3; 435/75; 435/252.1; 435/825
[58] Field of Search ............................ 435/71.3, 252.1, 435/75, 825

[56] References Cited

U.S. PATENT DOCUMENTS

| | | | |
|---|---|---|---|
| 3,067,099 | 12/1962 | McCormick et al. | 424/115 |
| 4,328,211 | 5/1982 | Sugawara et al. | 435/169 |
| 4,547,488 | 10/1985 | Merkel | 514/10 |
| 4,946,941 | 8/1990 | Kondo et al. | 435/71.3 |
| 5,312,738 | 5/1994 | Hamill et al. | 435/75 |

FOREIGN PATENT DOCUMENTS

| | | |
|---|---|---|
| 231111 | 8/1987 | European Pat. Off. . |
| 265071 | 4/1988 | European Pat. Off. . |

OTHER PUBLICATIONS

Tsuji et al., The Journal of Antibiotics, vol. XL1, No. 6. pp. 819–822 (Jun. 1988).

Primary Examiner—Herbert J. Lilling
Attorney, Agent, or Firm—Kathleen R. S. Page; Thomas G. Plant

[57] ABSTRACT

New glycopeptides prepared by biotransformation of a vancomycin-type antibiotic by an *Acinomadura citrea* culture (NRRL 18382), which are useful intermediates, and methods of preparing the biotransformed intermediates by adding a vancomycin-type glycopeptide to a growing culture of *Actinomadura citrea* NRRL 18382 and continuing fermentation under submerged aerobic conditions, are provided.

5 Claims, 3 Drawing Sheets

Figure 2
Fatty Acid Comparison of A87580 and Related Actinomadura Species

Figure 3
Dendrogram of A87580 and Related Actinomadura Species

BIOTRANSFORMATION OF GLYCOPEPTIDE ANTIBIOTICS

This application is a division of prior application Ser. No. 08/117,376, filed Sep. 3, 1993, abandoned which is a continuation of application Ser. No. 07/627,628, filed Dec. 13, 1990, now abandoned, which is a continuation of application Ser. No. 07/225,690, filed Jul. 28, 1988, now abandoned.

SUMMARY OF THE INVENTION

This invention relates to a new group of glycopeptide compounds which are prepared by biotransformation of a vancomycin-type antibiotic by an *Actinomadura citrea* culture. The biotransformation removes the N-terminal leucine moiety. The bioconverted compounds are useful intermediates which can be reacylated to restore antibacterial activity and thus may lead to improved antibiotics.

This invention also relates to methods of preparing the biotransformed intermediates by adding a vancomycin-type glycopeptide to a growing culture of *Actinomadura citrea* NRRL 18382 and continuing fermentation under submerged aerobic conditions until a substantial level of the intermediate is produced. The intermediate can be extracted from the fermentation broth by adsorption techniques.

Because *A. citrea* NRRL 18382 is a newly discovered strain, this invention further provides a biologically pure culture of this microorganism.

REFERENCE TO DRAWINGS

DETAILED DESCRIPTION OF THE INVENTION

Vancomycin-type glycopeptides are a valuable group of antibiotics. Vancomycin itself has been commercially successful because of its great value in treating diseases caused by resistant organisms. Unfortunately, organisms resistant to vancomycin have developed, and so the need for improved vancomycin-type compounds continues.

Illustrative members of the group of vancomycin-type glycopeptide antibiotics to which this invention relates are listed in Table I.

TABLE I

| Vancomycin-type Glycopeptide Antibiotics | |
| --- | --- |
| Antibiotic | Reference |
| vancomycin | U.S. Pat. No. 3,067,099, issued December 4, 1962 |
| M43D | U.S. Pat. No. 4,547,488, issued October 15, 1985 |
| A82846A, A82846B and A82846C | U.S. Pat. application Ser. No. 07/127,937 filed December 2, 1987 |
| Orienticin A (PA-42867-A), Orienticin B (PA-42867-B) and Orienticin D | European Patent Application No. 0231 111 (August 8, 1987; Derwent No. 87-117802/17); N. Tsuji et al., "New Glycopeptide Antibiotics I. The Structures of Orienticins", J. Antibiotics 41 (6) 819–822 (1988) |

For convenience in discussions herein, this group of compounds will be called vancomycin-type antibiotics.

Although some semi-synthetic derivatives of glycopeptide antibiotics have been reported, little information exists on the bioconversion of these compounds. The only studies to date have been on the aridicins, in which protoplasts of the producing culture, *Kibdelosporangium aridum*, have been shown to add sugars to the aglycone of the peptide core.

The mode of action of this class of antibiotics is to interfere with cell-wall formation by binding to terminal D-alanyl-D-alanine moieties of the developing bacterial cell wall. Mechanism of action studies have shown that amide nitrogens at the N-terminus of the antibiotic form a "carboxylate binding pocket" that secures the carboxylate group of terminal D-alanyl-D-alanine. The phenol-phenol coupling of the aromatic groups of the antibiotic aid in maintaining the proper pocket conformation. Removal of the N-methyl-leucine group of vancomycin B would have two effects. It would disrupt the binding pocket, possibly resulting in a molecule devoid of antibacterial activity. This would provide a core molecule which could be chemically modified to restore and perhaps enhance the biological activity of this class of compounds.

Schabel et al. (A. A. Schabel, K. E. Merkel, H. M. Higgens, K. H. Michel, J. S. Ott and R. Nagarajan, 26th Interscience Conference on Antimicrobial Agents and Chemotherapy, New Orleans, La., Sep. 28–Oct. 1, 1986, Abstract No. 225) were able to remove the N-methylleucine group from aglucovancomycin by Edman degradation, and this product did not have antibacterial activity. The Edman conditions, however, removed the sugar groups from vancomycin itself.

We succeeded in removing the N-(N-methyl-D-leucine) and D-leucine groups from vancomycin-type antibiotics without affecting the labile sugar groups by biotransforming the parent antibiotic, using a culture of *Actinomadura citrea* NRRL 18382. As suggested by the mode of action of the glycopeptides and by the work of Schabel et al., the de-(leucyl) products were devoid of antibacterial activity.

We further succeeded in reacylating the novel intermediates with leucine to restore antibacterial activity, thereby verifying the usefulness of the novel intermediates.

The glycopeptide compounds of this invention have the structure shown in formula 1:

wherein

X and Y independently are H or Cl;

R is selected from H, D-leucyl, (mono-, di- or tri-N-methyl)-D-leucyl, protected-D-leucyl or protected-(mono-, di- or tri-N-methyl)-D-leucyl;

$R^1$ is selected from H, vancosaminyl, 4-epi-vancosaminyl or L-olivosyl;

$R^{1^a}$ is selected from H or 4-epi-vancosaminyl; provided that 1) when $R^{1^a}$=H, $R^1$ must be vancosaminyl or H and both X and Y must be Cl; 2) when X=H, $R^1$ must be 4-epi-vancosaminyl; 3) when $R^1$=L-olivosyl, X must be Cl, Y must be H and $R^{1^a}$ must be 4-epi-vancosaminyl; 4) when R=D-leucyl, X and Y=Cl and $R^{1^a}$=H, $R^1$ cannot be vancosaminyl; 5) when R=N-methyl-D-leucyl, $R^1$ cannot be 4-epi-vancosaminyl; 6) when R=N-methyl-D-leucyl and $R^1$=vancosaminyl, one of X or Y must be other than H; 6) when R=N-methyl-D-leucyl and $R^1$=L-olivosyl, either $R^{1^a}$ or Y must be other than H; 7) when R=di-(N-methyl)-D-leucyl and $R^{1^a}$=H, $R^1$ cannot be vancosaminyl; 8) when R=di-(N-methyl)-D-leucyl, $R^{1^a}$=4-epi-vancosaminyl, and X=Cl, Y cannot be H; and 9) when R=tri-(N-methyl)-D-leucyl, $R^{1^a}$ cannot be H; or a salt thereof.

The formula 1 compounds wherein R is hydrogen (the 1a compounds) are prepared by biotransformation of a vancomycin-type compound of formula 2:

wherein $R^2$=hydrogen or methyl, and $R^1$, $R^{1^a}$, X and Y are as defined, supra.

The formula 1 compounds can form salts, which are also part of this invention. The salts are useful, for example, for separating and purifying the compounds.

The salts are prepared using standard procedures for salt preparation. For example, the compounds can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methane-sulfonic, benzensulfonic, sorbic, picric, benzoic, cinnamic and like acids.

Pharmaceutically acceptable acid addition salts are an especially preferred group of salts of this invention.

The terms "protected-D-leucyl" or "protected- (mono-, di- or tri-N-methyl)-O-leucyl" refer to a D-leucyl or (mono-, di- or tri-N-methyl)-D-leucyl group in which the free amino group is protected by an art-recognized amino-protecting group. Art workers will recognize that the protecting group must be compatible with the other functional groups in the molecule. Preferred amino-protecting groups are those which can be readily removed subsequently. Examples of suitable protecting groups can be found in "Protective Groups in Organic Synthesis" by Theodora W. Greene, John Wiley and Sons, N.Y. 1981, Chapter 7. An especially preferred amino-protecting group is the tert-butoxycarbonyl (t-BOC) group.

This invention further provides a process for bioconverting a vancomycin-type glycopeptide compound which comprises 1) cultivating *Actinomadura citrea* NRRL 18382, or a mutant thereof which removes D-amino acids from vancomcyin-type glycopeptides, in a culture medium containing assimilable sources of carbon, nitrogen, and inorganic salts under submerged aerobic fermentation conditions 2) adding the compound to the growing culture and 3) continuing the fermentation until a recoverable amount of bioconverted compound is produced.

The biotransformation is accomplished, therefore, by adding a formula 2 compound to the growing *Actinomadura citrea* culture and continuing fermentation until a recoverable amount of the corresponding 1a compound is formed. The bioconversion is remarkably efficient. For example, vancomycin has consistently been converted by the *A. citrea* culture at a rate of 90% or better.

The exact mechanism by which the culture carries out the biotransformation is unknown, but preliminary work has indicated that the organism does not produce a D-leucine amino-peptidase.

For convenience, the new microorganism of this invention, which removes D-leucine or N-methyl-D-leucine from vancomycin-type glycopeptides, is called culture A87580. Culture A87580 was isolated from a soil sample from Indonesia.

A culture of the A87580 organism was deposited and made part of the stock culture collection of the Northern Regional Research Center, Agricultural Research, North Central Region, 1815 North University Street, Peoria, Ill., 61604, on Jul. 7, 1988. The culture is available to the public from that depository under the accession number NRRL 18382.

Taxonomic studies of this culture were carried out by Frederick P. Mertz of the Lilly Research Laboratories. Based on these studies, the new organism is classified as a strain of *Actinomadura citrea*. This classification is based on laboratory comparison with similar species and comparison of A87580's characteristics with published descriptions of the characteristics of similar species.

Methods Used

These studies were made using methods recommended by the International Streptomyces Project (ISP) for the characterization of Streptomyces species [E. B. Shirling and D. Gottlieb, "Methods for Characterization of Streptomyces Species," *Int. J. Syst. Bacteriol.* 16:313–340 (1966)], as well as methods given by Gordon [R. E. Gordon, D. A. Barnett, J. E. Handerhan, and C. Pang, "Nocardia coeliaca, Nocardia autotrophica, and the Nocardin Strain," *Int. J. Syst. Bacteriol.* 24:54–63 (1974)].

Starch hydrolysis was determined by testing for the presence of starch with iodine on ISP No. 4 (inorganic salts-starch agar) plates.

NaCl tolerance was measured by adding NaCl to ISP No. 2 agar to equal the concentration desired.

ICSS-NBS Centroid Color Charts, standard sample No. 2106 (National Bureau of Standards, 1958, U.S. Department of Commerce, Washington, D.C.) and the Color Harmony Manual (4th ed., Container Corporation of America, Chicago, Ill., 1958) were used to assign color names to the reverse side and to aerial hyphae, respectively.

Morphology was studied using an optical light microscope and a scanning electron microscope (SEM).

The isomers of diaminopimelic acid (DAP) and the carbohydrates in hydrolysates of whole cells were established by the chromatographic methods of Becker et al. [B. Becker, M. P. Lechevalier, R. E. Gordon, and H. E. Lechevalier, "Rapid Differentiation between Nocardia and Streptomyces by Paper Chromatography of Whole-cell Hydrolysates," *Appl. Microbiol.* 12:421–423 (1964)] and of Lechevalier et al. [M. P. Lechevalier and H. Lechevalier In *A University Laboratory Approach*, Dietz and Thayer (eds.), Special Publication No. 6, Society for Industrial Microbiology, Arlington Va., 1980; pp. 277–284].

Resistance to antibiotics was measured by padding antibiotic sensitivity discs onto the surface of seeded ISP No. 2 agar plates. Resistance was scored as (+) when no zone of inhibition was observed and as (−) when a zone of inhibition was observed.

Whether mycolic acids were present was determined by a method based on techniques described by D. E. Minnikin, L. Alshamaony and M. Goodfellow ["Differentiation of Mycobacterium, Nocardia, and Related Taxa by Thin-Layer Chromatographic Analysis of Whole-organism Methanolysates," *J. Gen. Microbiol.* 88:200–204 (1975)].

Phospholipids were determined by the procedures of:

1) M. P. Lechevalier A. E. Stern and H. A. Lechevalier, "Phospholipids in the Taxonomy of Actinomycetes," Actinomycetes, K. P. Schaal and G. Pulverer (eds); Zbl. Bakt. Suppl. 11, Gustav Fischer Verlag, Stuttgart, N.Y., 1981];

2) D. E. Minnikin, I. G. Hutchinson and A. B. Caldicott, "Thin-layer Chromatography of Methanolysates of Mycolic Acid-containing Bacteria," *J. Chromatography* 188:221–233 (1980); and 3) J. C. Dittmer and R. L. Lester, "A Simple, Specific Spray for the Detection of Phospholipids on Thin-layer Chromatograms, *J. Lipid Research* 5(1):126–128 (1964).

Menaquinone composition was determined by following the procedures of

1) R. M. Kroppenstedt in *Chemical Methods in Bacterial Systematics*, M. Goodfellow and D. E. Minnikin (eds.), 1985, pp. 173–196; and 2) M. D. Collins; ibid, pp. 267–285.

Fatty acid analysis was done using the HP 5898A Microbial Identification System (See L. Miller and T. Berger, "Bacterial Identification by Gas Chromatography of Whole Cell Fatty Acids", Hewlett-Packard Application Note 228–241, 1985; 8 pp). Fatty acid methyl esters were made from lyophilized whole cells grown under identical conditions.

Cultural Characteristics

Culture A87580 grew well on both complex and defined media. Aerial hyphae were produced on most of the media used. The aerial-spore-mass color was pale yellow to grayish-yellowish pink, or a light bluish gray, depending on the medium. The reverse side was a distinctive reddish orange. This pigment was not subject to change with pH. A distinctive lemon-yellow soluble pigment was released into the medium.

The cultural characteristics are summarized in Table I.

TABLE I

Cultural Characteristics of A87580 on Various Agar Media[a]

| Agar Media | A87580 Characteristics[b] |
|---|---|
| ISP No. 2 | G: Abundant<br>R: 54.brO<br>Am: Good:pale Yellow<br>Sp: Lemon-yellow |
| ISP No. 3 | G: Good<br>R: 53.m.O<br>Am: Good:l. bluish Gray<br>Sp: Lemon-yellow |
| ISP No. 4 | G: Abundant<br>R: 38.d.rO<br>Am: Good:l. bluish Gray<br>Sp: None |
| ISP No. 5 | G: Abundant<br>R: 35.s.rO<br>Am: Abundant:m.yPk<br>Sp: None |
| ISP No. 7 | G: Abundant<br>R: 51.deep O<br>Am: Abundant:l.yPk<br>Sp: Lemon-yellow |
| ATCC No. 172 | G: Good<br>R: 51.deep O<br>Am: Good:l. bluish Gray<br>Sp: Lemon-yellow |
| Bennett's | G: Abundant<br>R: 48.v.O<br>Am: Good:pale Yellow<br>Sp: Lemon-yellow |
| Calcium malate | G: Good<br>R: 54.brO<br>Am: Good:pale Yellow<br>Sp: Lemon-yellow |
| Jensen's | G: Good<br>R: 53.m.O<br>Am: Fair:gy. yPk<br>Sp: Light Yellow |
| Nutrient | G: Good<br>R: 39.gy.rO<br>Am: Fair:gy. yPk<br>Sp: None |
| Tap Water Agar | G: Fair<br>R: 10. pk Gray<br>Am: Fair: gy. yPk<br>Sp: None |
| Anio-Hensen's | G: Good<br>R: 51.deep O<br>Am: Good:i. bluish Gray<br>Sp: Light Yellow |
| Tomato Paste-Oatmeal | G: Abundant<br>R: 53.m.O<br>Am: Good:pale Yellow<br>Sp: Lemon-yellow |
| Czapek's | G: Good<br>R: 8.gy Pink<br>Am: Good:l. bluish Gray<br>Sp: None |

[a]When incubated at 30° C. for 14 days
[b]G = growth; R = reverse; Am = aerial mycelium; Sp = soluble pigment Morphological Characteristics Culture A87580 produced an extensive substrate mycelium. Well-formed aerial hyphae were present on most of the media used. Sporophores with clusters of tightly formed spore chains were arranged as hooks and loops in typical Rectus-flexibilis (RA) morphology. The spore shape is spherical; spore size averages 1.0 μm in diameter; and the spore surface has a distinctive warty appearance. The spore chains contain less than 10 spores per chain.

Physiological Characteristics culture A87580 produced acid from the following carbohydrates: adonitol, L-arabinose, cellobiose, fructose, glucose, glycerol, glycogen, inositol, maltose, mannitol, rhamnose, trehalose and xylose. A87580 did not produce acid from: D-arabinose, cellulose, dextrin, dulcitol, ethanol, erythritol, galactose, inulin, lactose, mannose, melizitose, melibiose, alpha-methyl-D-glucoside, raffinose, ribose, salicin, sorbitol, sorbose, sucrose and xylitol.

Culture A87580 utilized the following organic acids (as sodium salts): acetate, citrate, propionate and pyruvate. It did not utilize benzoate, butyrate, formate, lactate, malate, mucate, oxalate, succinate and tartrate.

A87580 decomposed casein, elastin, esculin, hypoxanthine, starch, testosterone, tyrosine and urea, but did not decompose adenine, allantoin, calcium malate, guanine, hippurate or xanthine.

A87580 produced catalase, phosphatase, urease and $H_2S$. It liquified gelatin, reduced nitrates, hydrolyzed skim milk and was able to survive at 50° C. for 8 hours. It did not produce melanoid pigments.

Culture A87580 grew at temperatures between 15 and 40° C. The culture tolerated NaCl at levels up to and including 7%.

A87580 was resistant to cephalothin (30 μg), lincomycin (2 μg), penicillin G (10 units), rifampin (5 μg) and lysozyme (50 μg/mL). It was sensitive to bacitracin (10 units), gentamicin (10 μg), neomycin (30 μg), oleandomycin (15 μg), streptomycin (10 μg), tetracycline (30 μg), tobramycin (10 μg) and vancomycin (30 μg).

Cell-Wall Analysis

Hydrolyzed whole cells of A87580 contained meso-diaminopimelic acid. The following sugars were detected in the whole cell extracts: galactose, glucose, mannose and madurose. Thus, A87580 has a type III cell wall and a type B sugar pattern [See M. P. Lechevalier and H. Lechevalier, "Chemical Composition as a Criterion in the Classification of Aerobic Actinomycetes", *Int. J. Syst. Bacteriol.* 20:435–443 (1970)].

Mycolic acids were not detected.

Phospholipid determinations on the whole cells indicated the presence of phosphatidyl inositol, diphosphatidyl glycerol and GluNu (an unknown structure containing glucosamine). Neither phosphatidyl ethanolamine nor phosphatidyl choline was detected. Therefore, A87580 has a type IV phospholipid pattern [See M. P. Lechevalier, A. E. Stern and H. A. Lechevalier, supra].

The menaquinones detected in A87580 were hexahydrogenated menaquinones with nine isoprene units, MK-9($H_6$) and minor amounts of tetrahydrogenated and octahydrogenated menaquinones, MK-9($H_4$) and MK-9($H_8$), respectively.

Identity of Strain A87580

The chemotaxonomic properties and the cultural and morphological characteristics of A87580 support the assignment of this isolate to the genus Actinomadura (See V. B. D. Skerman, V. McGowan, and P. H. A. Sneath, *Approved Lists of Bacterial Names*, American Society for Microbiology, Washington D.C., 1980).

Twenty-two type strains of Actinomadura species were grown along with culture A87580 on 21 different agar media. Cultural and morphological characteristics were compared. Culture A87580 showed similarity to *Actinoma-*

*dura citrea* on many media. The similarity was especially noted on calcium-malate, Bennetts and tomato paste-oatmeal (TPO) agar. A strong lemon-yellow soluble pigment was observed only with A87580 and *A. citrea*.

Biochemical characteristics of a number of species were gathered from the literature [M. Athalye, M. Goodfellow, J. Lacey, and R. P. White, "Numerical Classification of Actinomadura and Nocardiopsis," *Int. J. Syst. Bacteriol.* 35: 86–98 (1985)]. These characteristics were compared with those of A87580 by constructing Table II, which compares similarity coefficients. The coefficient of Jaccard Sj, and the simple matching coefficient $S_{sm}$ were used (W. Kurylowicz, A. Paszkiewicz, W. Woznicka, W. Kurzatkowski and T. Szulga, *Numerical Taxonomy of Streptomycetes*, Polish Medical Publishers, Warsaw, 1975, p. 37).

TABLE II

Comparison of A87580 with Several
Actinomadura Species Using Similarity Coefficients[a]

| Culture | Sj | $S_{sm}$ |
|---|---|---|
| A87580 | 100 | 100 |
| A. citrea | 78 | 84 |
| A. rubra | 75 | 81 |
| A. cremea | 65 | 76 |
| A. luteofluorescens | 67 | 74 |
| A. verrucosospora | 66 | 72 |
| A. salmonea | 63 | 72 |
| A. roseloa | 51 | 58 |

[a]Data for *A. coerulea* was unavailable.

Fatty acid analyses were performed on the whole cells of A87580 and seven other species that have a warty spore-surface ornamentation and other similarities with A87580.

Figure 1:
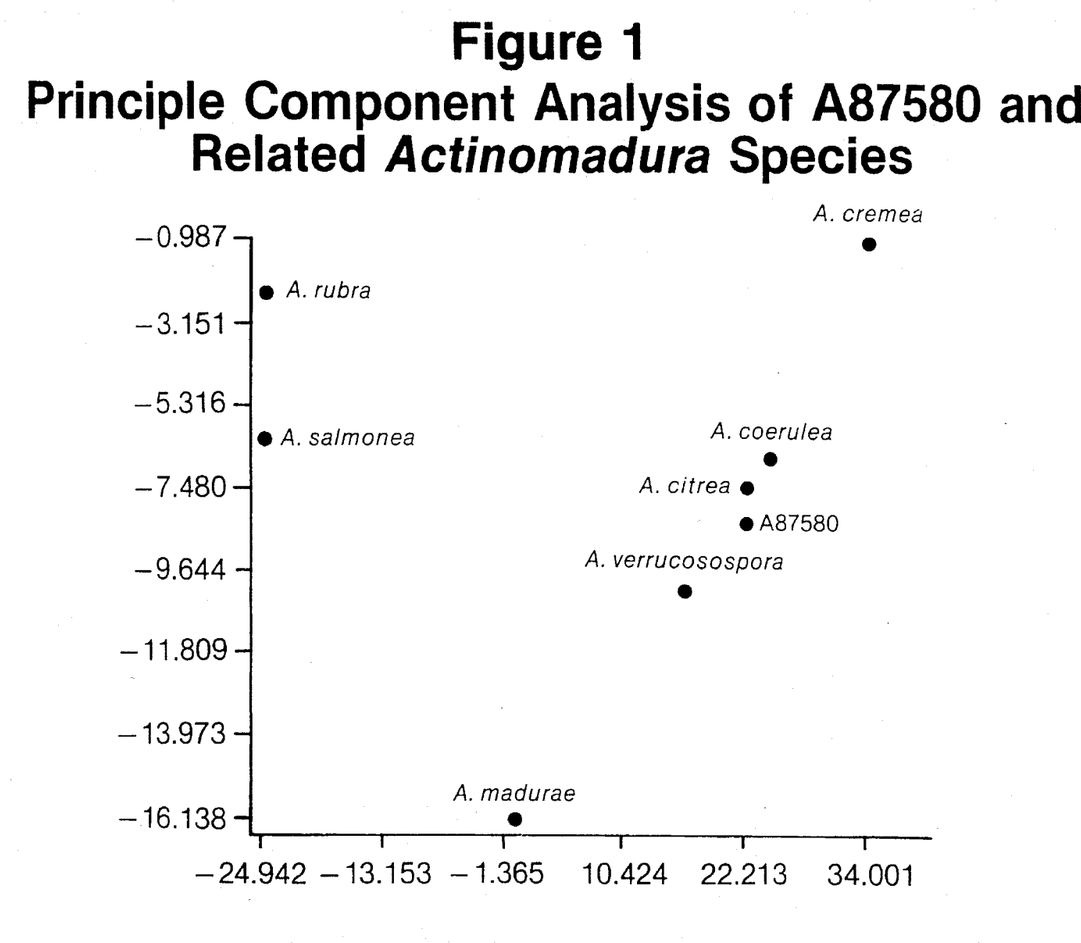
FIG. 1 is a principle component analysis of culture A87580 and related Actinomadura species.
Figure 2:
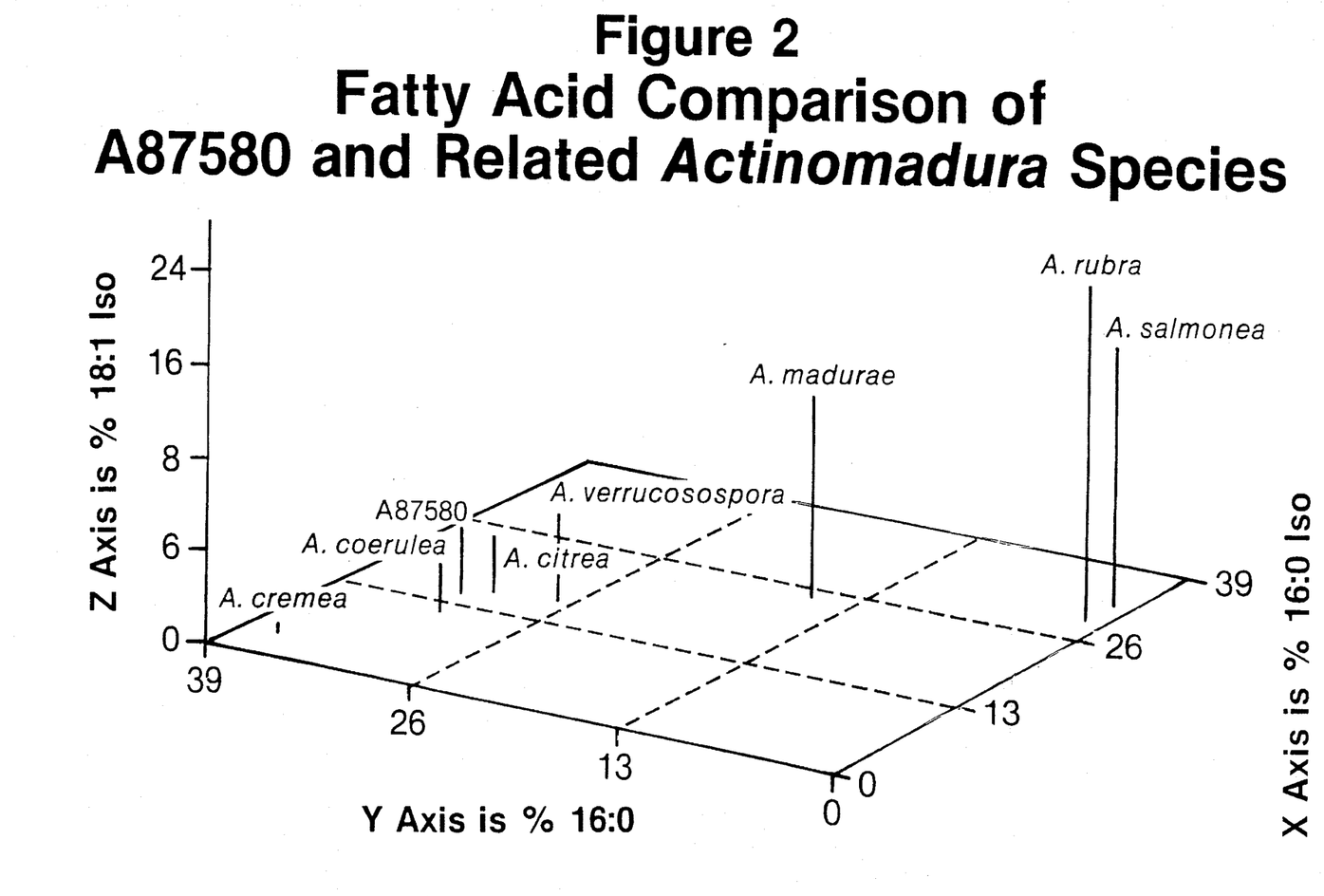
FIG. 2 compares the fatty acids present in culture A87580 and related Actinomadura species.
Figure 3:
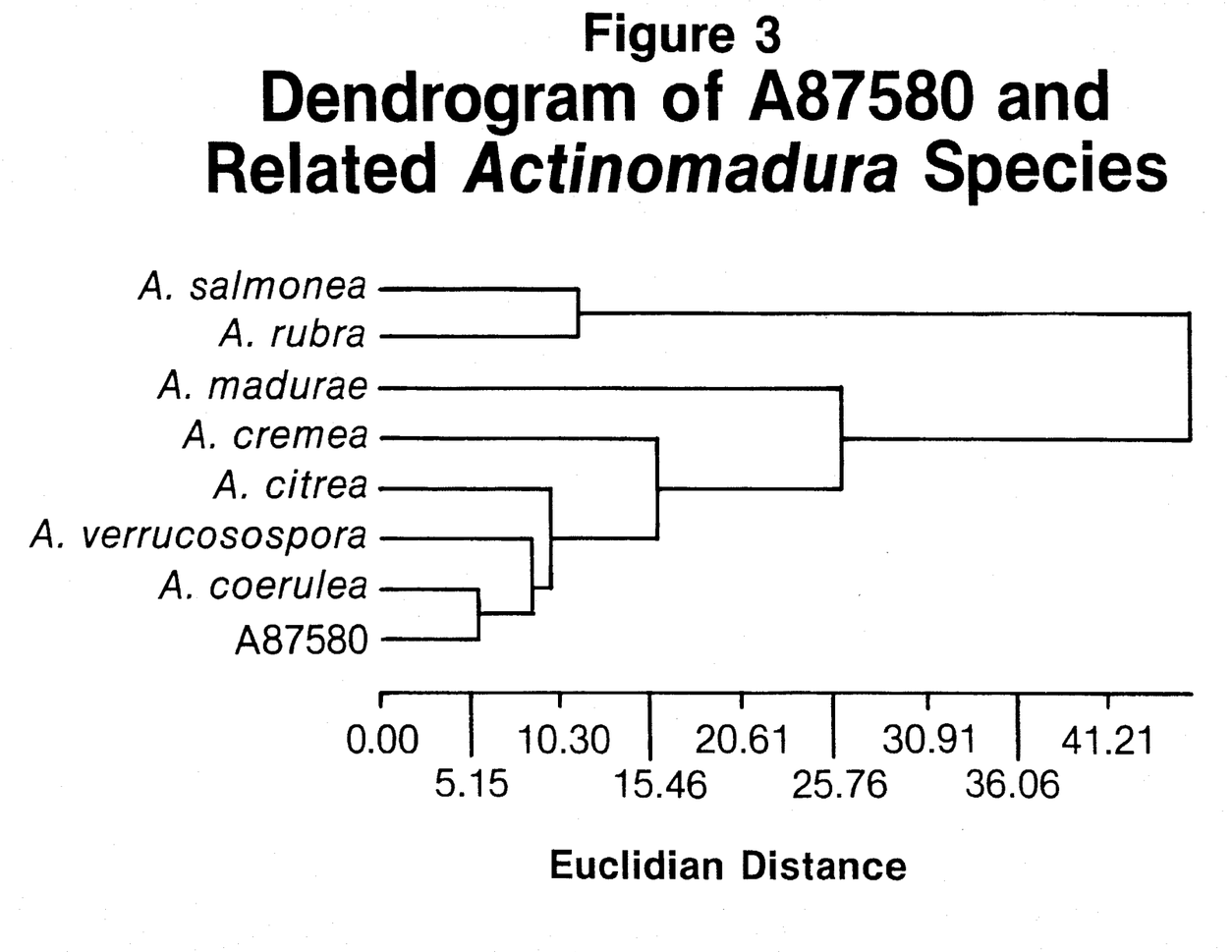
FIG. 3 is a dendrogram obtained from the fatty acid analysis of A87580 and other Actinomadura species.

A principle component analysis, a 3-D plot showing named fatty acids and a dendrogram obtained from this data are shown in FIGS. 1, 2 and 3, respectively.

The principle component analysis is two dimensional and was computer generated. Units of measurement in the principle component plot are standard deviations. The dendrogram was based on Euclidian distance and was also computer generated.

FIG. 1 shows that culture A87580, *Actinomadura citrea*, *A. coerulea*, and *A. verrucosospora* form a distinct cluster by themselves. This is also clearly illustrated by the dendrogram.

The cultural characteristics, biochemical properties, similarity coefficients and fatty acid analyses indicate that, of the known species with which it was compared, A87850 shares the most characteristics with *Actinomadura citrea*.

The differences between A87850 and *A. citrea* are not sufficient to establish a new species and are considered to be strain differences. Table III shows the differences between A87850 and *A. citrea*.

TABLE III

Differences Between A87580 and *A. citrea*

| Characteristic | A87580 | A. citrea[a] |
|---|---|---|
| Guanine hydrolysis | − | (+) |
| Starch hydrolysis | + | (−) |
| Acid produced from: | | |
| Dextrin | − | + |
| Lactose | − | + |
| Mannose | − | + |
| Sucrose | − | + |
| Tolerates 7% NaCl | + | − |

[a]() = not consistent

This study supports the conclusion that culture A87580 is a new strain of *Actinomadura citrea*.

As is the case with other organisms, the characteristics of *Actinomadura citrea* are subject to variation. Mutants of the strain may be obtained by methods known in the art, for example, by treatment with various physical and chemical mutagens such as ultraviolet light, X rays, gamma rays and chemicals such as N-methyl-N'-nitro-N-nitrosoguanidine. Natural and induced mutants of *Actinomadura citrea* NRRL 18382 which retain its characteristic capacity to remove D-amino acids from vancomycin-type glycopeptides are considered part of this invention.

The culture medium used to grow the *Actinomadura citrea* culture can be any one of a number of media. For economy in production, optimal yield, and ease of product isolation, however, certain culture media are preferred. Thus, for example, preferred carbohydrate sources are dextrose and potato dextrin, although glucose, xylose, fructose, galactose, mannose, mannitol, soluble starch and the like can also be used.

A preferred nitrogen source is casein, although meat peptones, yeast extract, acid-hydrolyzed casein, beef extract, fish meal, liver meal, and the like can also be used.

Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. If foaming is a problem, small amounts (i.e. 0.2 ml/L) of an antifoam agent such as polypropylene glycol may be added to large scale fermentation media.

For large scale work, submerged aerobic fermentation in tanks is preferred. Smaller quantities may be handled by shake-flask culture. Because of the time lag commonly associated with inoculating large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media can also be used.

The *Actinomadura citrea* culture grows at temperatures between about 25° and about 37° C. An optimum temperature for the biotransformation appears to be about 30° C.

As is customary in submerged aerobic culture processes, sterile air is blown into the vessel from the bottom while the medium is stirred with conventional turbine impellers. In general, the aeration rate and agitation rate should be sufficient to maintain the level of dissolved oxygen at or above 30% of saturation.

The bioconversion can be followed during the fermentation by testing samples of the broth for antibiotic activity against organisms known to be sensitive to the antibiotic. One useful assay organism is *Bacillus subtilis* ATCC 6633. The bioassay is conveniently performed by the agar-well plate test.

Following the bioconversion, the 1a compounds can be recovered from the fermentation medium by methods used in the art. The 1a compounds occur mainly in the broth. Maximum recovery is accomplished, therefore, by initially filtering the medium to separate the broth from the mycelial mass.

The 1a compounds can be recovered from the filtered broth by a variety of techniques. A preferred technique involves adjusting the pH of the filtered broth to about 7 and adsorbing it onto a macroreticular resin, e.g. Diaion HP-20. The 1a compound can be eluted from the adsorbent with a suitable solvent, e.g. a methanol/water mixture.

The formula 1a compounds are useful intermediates which may be reacylated to give the compounds of formula 1 wherein R=D-leucyl, (mono-, di- or tri-N-methyl)-D-leucyl, protected-D-leucyl, or protected-(mono-, di- or tri-N-methyl)-D-leucyl (formula 1b compounds). Antibacterial activity is restored in the 1b compounds.

The 1b compounds are prepared from the 1a compounds using methods conventional in the art for forming an amide bond. Acylation is accomplished, in general, by reacting the 1a compound with an activated derivative corresponding to the acyl group ($R^2$).

The term "activated derivative" means a derivative which renders the carboxyl function of the acylating agent reactive to coupling with the primary amino group to form the amide bond which links the acyl group to the glycopeptide core. Suitable activated derivatives, their methods of preparation, and their methods of use as acylating agents for a primary amine will be recognized by those skilled in the art.

Preferred activated derivatives are: (a) an acid halide (e.g. an acid chloride), (b) an acid anhydride (e.g., an alkoxyformic acid anhydride) or (c) an activated ester (e.g. a 2,4,5,-trichlorophenyl ester). Other methods for activating the carboxyl function include reacting the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

Those skilled in the art will recognize that the formula 1 compounds wherein R is D-leucyl or (mono-, di, or tri-N-methyl)-D-leucyl) (formula 1c compounds) are prepared using selective acylation procedures and with the assistance of amino-protecting groups. Thus, the formula 1 compounds wherein R is protected-D-leucyl or protected-(mono-, di- or tri-N-methyl)-D-leucyl (the formula 1d compounds) are useful intermediates in making the 1c compounds.

The following non-limiting examples are provided to illustrate this invention. In these examples, these media are discussed:

TSBD Medium: T-soy broth base, 30 g; potato dextrin, 20 g; and 1 liter distilled water.

CSI Medium: Nutrisoy flour, 15 g; casein, 1.0 g; dextrose, 25 g; blackstrap molasses, 3.0 g; $CaCO_3$, 2.5 g; Czapeck's mineral solution, 2.0 mL; and 1 liter distilled water; adjust pH to 7.4

EXAMPLE 1

Cultivation of A87580

Use the culture *Actinomadura citrea* NRRL 18382, either as a lyophilized pellet or as a suspension maintained in liquid nitrogen, to inoculate TSBD medium. Allow the culture to grow for two days at 30° C. with shaking (250 rpm). Use this vegetative culture to inoculate CSI medium and incubate for two to four days growth at 30° C. and 250 rpm.

EXAMPLE 2

Bioconversion of Vancomycin

Add vancomycin (200 μg/mL, final concentration) to an A87580 culture, prepared as described in Example 1, and incubate until conversion is complete (usually about 24 to 48 hours).

Monitor the conversion by testing broth samples against a susceptible test organism, such as *Bacillus subtilis*, to determine the biological activity remaining.

When testing for biological activity, adjust the pH of the broth to 10.5 to extract the remaining antibiotic from the mycelia and remove the cells by centrifugation. Decant the supernatant and return the pH to 7.0. Disappearance of activity indicates that conversion is complete.

EXAMPLE 3

Isolation of N-De-(N-Methyl-D-Leucyl)-Vancomycin [Vancomycin Hexapeptide]

Fermentation broth (7 L) was prepared as described in Example 1. Vancomycin (2g) was added, and the fermentation was continued as in Example 2. The broth was filtered, using 3% Hyflo Supercel, the mycelial mat was discarded, and the pH of the filtrate was adjusted to 7.0 with 1.0N HCl.

HPLC analysis of the broth filtrate indicated that approximately 90% of the original vancomycin was converted to vancomycin hexapeptide.

The filtrate was applied to a column of Diaion HP-20 resin (6.0×53 cm) equilibrated in water. The column was washed with water (4.0 L) and eluted with three portions (850 mL each) of 50% methanol in water.

The eluate was concentrated to a residue which was redissolved in water (750 mL) and lyophilized to give 26 g of material. HPLC analysis showed the sample to be 5.3% pure, thus representing 1.4 g of vancomycin hexapeptide.

Crude product (1.5 grams @5.3% purity) prepared in this manner was dissolved in water (20 mL) and applied to a column of Sephadex CM-25 (2.8×50 cm; $NH_4^+$ cycle, equilibrated with water). The column was initially washed with water (60 mL) and then was eluted with a linear gradient using 500 mL each of water and 0.25M ammonium bicarbonate ($NH_4HCO_3$). The desired compound was eluted using a flow rate of 3.5 mL/min and collecting 15-mL fractions was eluted.

The fractions containing the product (#30–35) were pooled and applied to a column of Diaion HP-20 resin (1.2×30 cm, equilibrated in water). After loading, the column was washed with water (100 mL) to remove inorganic salts. The desired material was eluted from the column in a single 50-mL portion of 50% methanol in water (flow rate: 2 mL/min).

The HP-20 eluate was concentrated to a residue and redissolved in water (15 mL). It was necessary to lower the pH to effect solution. Lyophilization of this solution yielded 23 mg of purified vancomycin hexapeptide.

CHARACTERISTICS OF VANCOMYCIN HEXAPEPTIDE.

UV spectrophotometric analysis gave a lambda max. of 281 (ε=5,780) under neutral conditions (EtOH). FAB mass spectrometry gave a P+1 of 1321 (integer molecular weight is 1320). Calculated exact mass for $C_{59}H_{63}N_8O_{23}Cl_2$ is: theory, 1321.3383 and found, 1321.3374. First order interpretation of the 300 MHz proton NMR demonstrated the absence of the alpha (3.70 ppm), beta (1.65, 1.5 ppm) and gem-dimethyl protons (0.9 ppm) of leucine.

EXAMPLE 4

HPLC System For Separation of Vancomycin and Its Hexapeptide

HPLC was performed using a $C_{18}$ (IBM Octadecyl, 4.5×150 mm, 5μ) column and a gradient system consisting of methanol (solvent A) and 0.05M ammonium trifluoroacetate at pH 3.0 (solvent B). The gradient started with 5% solvent A and 95% solvent B. From 1 to 11 minutes, the percent of A rose to 35 and was held there until the end of the run (19 minutes). The flow rate was 1 mL/minute, and the UV detector was set at 260 nm.

Using this system, vancomycin and its hexapeptide have the following approximate retention times:

|  | Minutes |
| --- | --- |
| Vancomycin: | 16.3 |
| Vancomycin hexapeptide: | 11.1 |

EXAMPLE 5

Reacylation and Deblocking of Vancomycin Hexapeptide

Vancomcyin hexapeptide (100 mg; 0.075 mmol) was dissolved in anhydrous DMF (5 mL), and N-(t-Boc-D-leucyl)-O-benzotriazole (50 mg; 0.14 mmol) was added. After 20 minutes at ambient temperature under nitrogen, TLC indicated that the reaction was complete. Removal of solvent and trituration with diethyl ether/methylene chloride (1/1), followed by filtration, yielded 118 mg of a tan glass.

FAB mass spectrum of the compound gave P+1 of 1534 (integer molecular weight=1533, emp. formula of $C_{70}H_{81}N_9O_{26}Cl_2$). Proton NMR showed that the leucine protons had been re-introduced.

The compound was then purified on a micro-preparative column (Waters $C_{18}$ μBondapak, 19×50 mm), using 25% acetonitrile/water containing 1% $NH_4H_2PO_4$, and desalted over HP-20 ss to give 22 mg of N-(t-Boc)-A51568A [N-(t-Boc-N-demethyl)-vancomycin].

This material was deblocked by adding trifluoroacetic acid (3 mL) to 20 mg of the compound at −10° C. with stirring. After 15 minutes at −10° C., the solvent was removed and the resulting syrup was triturated with methylene chloride (3×10 mL). The precipitate was redissolved in water; the pH was adjusted to 6.2 with pyridine; and the solution was lyophilized, yielding 12 mg of a tan solid.

FAB mass spectrum of a sample of the product gave P+1 of 1434. A diagnostic peak at 1128 was also found. This corresponds to the aglycone of A51568A which confirmed that acylation occurred at the N-terminus of the peptide core and not on the amino-sugar nitrogen. Exact mass for $C_{65}H_{75}N_9O_{24}Cl_2$ is: theory, 1434.4224 and found, 1434.4191.

Amino acid analysis showed the presence of one leucine for every aspartic acid in the molecule. Bioautography on TLC gave a single bioactive spot with the same Rf (0.4) as that of A51568A against *Micrococcus luteus*.

EXAMPLE 6

Biotransformation of A51568A to Vancomycin Hexapeptide

Fermentation broth (3 L) was prepared as described in Example 1; 200 mg of A51568A was added; and the fermentation was continued as in Example 2.

The whole broth was filtered using 3% Hyflo Supercel. The mycelial mat was discarded, and the pH of the filtrate was adjusted to 7.0 with 1.0N HCl.

The filtrate was applied to Diaion HP-20 resin (4.3×60 cm column) equilibrated in water. The column was washed with water (3.7 L) and eluted with 25% methanol in water (800 mL). The eluate was concentrated to a volume of 100 mL and applied to a column of Sephadex CM-25 (2.5×50 cm; $NH_4+$ cycle, equilibrated with water). The column was initially washed with water and then was eluted with a linear gradient using 300 mL each of water and 0.5M ammonium bicarbonate ($NH_4HCO_3$), collecting 20-mL fractions. Fractions containing the desired compound (#20 to #30) were pooled, concentrated to a volume of 20 mL and lyophilized to give 98.9 mg of vancomycin hexapeptide.

EXAMPLE 7

Preparation of N-de(N-Methyl-D-Leucyl)A82846B (A82846B Hexapeptide)

A82846B (200 mg) was added to fermentation broth (2 L) prepared as described in Example 1. The culture was incubated as described in Example 2 and then filtered using 3% Hyflo Supercel. The mycelial mat was discarded, and the pH of the filtrate was adjusted to 7.0 with 1.0N HCl.

The filtrate was applied to a column of Diaion HP-20 resin (4.2×60 cm) equilibrated in water. The column was washed with water (1.2 L) and eluted with 1 liter each of 25% and 50% methanol in water and 100% methanol.

The 50% eluate was concentrated to a volume of approximately 150 mL and lyophilized to give 527 mg of material. This material was shown by HPLC analysis to be approximately 18% pure, thus representing 95 mg of A82846B hexapeptide.

The 100% methanol eluate was concentrated, reconstituted in water (100 mL) and lyophilized to yield 814 mg of dry material. This product was shown by HPLC analysis to be approximately 8.8% pure, thus containing approximately 71 mg of the hexapeptide.

The 50% eluate product (527 mg @18% purity) was dissolved in water (10 mL) and applied to a column of Sephadex CM-25 (2.5×50 cm; $NH_4+$ cycle, equilibrated with water). The column was initially washed with water (50 mL) and then eluted with a linear gradient, using 500 mL each of water and 0.5M ammonium bicarbonate ($NH_4HCO_3$) at a flow rate of 3.5 mL/min and collecting 15-mL fractions. Fractions containing the desired compound (#72 to #86) were pooled, concentrated to a volume of about 40 mL and lyophilized to give 46.5 mg of A82846B hexapeptide.

FABMS: 1464 (P+1), integer mol. wt. is 1463 for $C_{66}H_{75}N_9O_{25}Cl_2$; peak match gave: theory, 1464.4324; found, 1464.42985. Amino acid analysis gave: asp (1), and no N-methyl-leucine. UV analysis (EtOH): λ max 281 nm (ε=5,640) neutral; λ max 307 (ε=10,100) base. 300 MHz PMR supports loss of N-methyl-leucine.

We claim:

1. A process for bioconverting a vancomycin-type glycopeptide compound of the formula wherein X and Y independently are H or Cl;

$R^2$ is H or methyl;

$R^1$ is selected from H, vancosaminyl and 4-epi-vancosaminyl;

$R^{1a}$ is selected from H and 4-epi-vancosaminyl;

provided that 1) when $R^{1a}$=H, $R^1$ must be vancosaminyl or H and both X and Y must be Cl; and 2) when X=H, $R^1$ must be 4-epi-vancosaminyl;

which comprises 1) cultivating *Actinomadura citrea* NRRL 18382, or a mutant thereof capable of removing D-amino acids from the vancomycin-type glycopeptide compound, in a culture medium containing assimilable sources of carbon, nitrogen, and inorganic salts under submerged aerobic fermentation conditions 2) adding the vancomycin-type glycopeptide compound to the growing culture and 3) continuing the fermentation until a recoverable amount of a bioconverted compound of the formula wherein X, Y, $R^1$, and $R^{1a}$ are as hereinabove defined, is produced.

2. The process of claim 1 which includes the additional step of separating the bioconverted compound from the culture medium.

3. The process of claim 1 wherein *A. citrea* NRRL 18382 is used.

4. A biologically pure culture of *Actinomadura citrea* NRRL 18382, or a mutant thereof which removes D-amino acids from vancomycin-type glycopeptide compounds.

5. The culture of claim 4 which is *Actinomadura citrea* NRRL 18382.

* * * * *